United States Patent [19]

Wang et al.

[11] 4,204,007
[45] May 20, 1980

[54] 4-(DIHYDROXYHEXOXY)DIHYDROCHALCONE SWEETENERS

[75] Inventors: Patricia C. Wang; Robert E. Wingard, Jr.; Guy A. Crosby, all of Palo Alto, Calif.

[73] Assignee: Dynapol, Palo Alto, Calif.

[21] Appl. No.: 964,211

[22] Filed: Dec. 1, 1978

Related U.S. Application Data

[63] Continuation-in-part of Ser. No. 863,116, Dec. 22, 1977, abandoned.

[51] Int. Cl.² .............................................. A23L 1/236
[52] U.S. Cl. ..................................... 426/548; 426/576; 426/590; 260/511
[58] Field of Search ............... 426/548, 804, 576, 590; 260/511

[56] References Cited

U.S. PATENT DOCUMENTS

| | | | |
|---|---|---|---|
| 3,974,299 | 8/1976 | Crosby et al. | 426/548 |
| 4,055,678 | 10/1977 | Crosby et al. | 426/548 |
| 4,092,346 | 5/1978 | Farkas et al. | 426/548 X |

FOREIGN PATENT DOCUMENTS 1196  1/1973  Hungary .................................. 426/548

*Primary Examiner*—Raymond N. Jones
*Assistant Examiner*—Esther M. Kepplinger
*Attorney, Agent, or Firm*—William H. Benz

[57] ABSTRACT

Dihydrochalcones of the formula

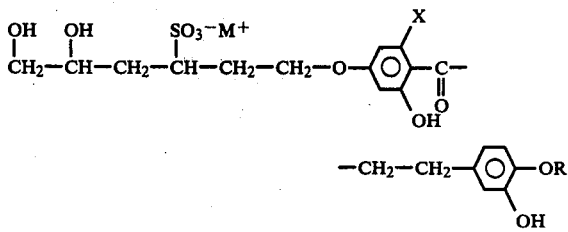

are disclosed wherein $M^+$ is a cation, X is H or OH, and R is a lower alkyl. These materials are useful as sweeteners for edibles. They may be prepared by electrophilic addition of the 3-sulfo-5,6-dihydroxyhexyl group to the corresponding flavanones, using epoxysultone, and thereafter converting to the dihydrochalcone.

11 Claims, No Drawings

4-(DIHYDROXYHEXOXY)DIHYDROCHALCONE SWEETENERS

This is a continuation-in-part of U.S. Pat. Application Ser. No. 863,116, filed on Dec. 22, 1977 now abandoned.

STATEMENT OF THE INVENTION

We have now discovered a group of new dihydrochalcones which have attractive sweetener properties. These materials, which are classifiable as 4-(dihydroxyhexoxy)-dihydrochalcones, are represented structurally as shown in General Formula I.

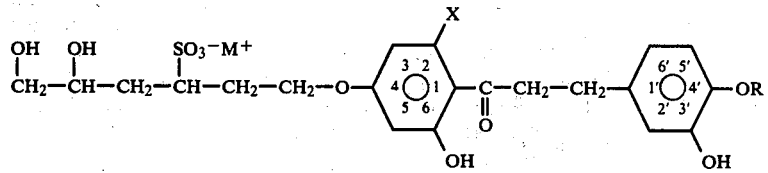

BACKGROUND OF THE INVENTION

1. Field of the Invention

This invention concerns synthetic sweeteners. More particularly, it concerns a new group of dihydrochalcone compounds and their use as sweeteners for edible compositions such as foodstuffs.

2. Background

Dihydrochalcones are compounds having a

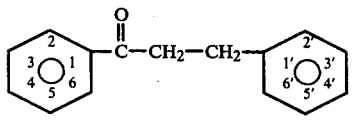

basic structure. A number of such compounds, both natural and synthetic, have been disclosed in the prior art. These materials vary from one another by the nature and placement of substituents on the aromatic rings.

In 1963, dihydrochalcones took on increased importance when it was discovered that some, but by no means all, of their number are sweet (Horowitz and Gentili, U.S. Pat. No. 3,087,871, issued Apr. 30, 1963). The earliest examples of sweet dihydrochalcones were derived from naturally occurring materials (flavanones) having saccharide residues attached at position four. More recently, applicants, their coworkers, and others have disclosed several sweet dihydrochalcones having smaller and simpler substituents at their four position as evidenced by: Rizzi, U.S. Pat. No. 3,855,301, issued Dec. 17, 1974; Rizzi, U.S. Pat. No. 3,751,270, issued Aug. 7, 1973; Farkus et al., U.S. Pat. No. 3,956,375, issued May 11, 1976; Crosby et al., U.S. Pat. No. 3,974,229, issued Aug. 10, 1976; Crosby et al., U.S. Pat. No. 3,976,790, issued Aug. 24, 1976; and Crosby et al., U.S. Pat. No. 4,055,678, issued Oct. 25, 1977. This work has repeatedly confirmed the empirical nature of the taste-chemical structure relationship. The exact nature of substituents and their placement on the molecule are critical. A change which is minor on its face may have a major effect on the taste properties of the dihydrochalcone. Two taste-related major goals of dihydrochalcone sweetener research are: (1) To provide compounds having solubility in aqueous media adequate to form suitably sweet consumer products; and (2) To eliminate, or at least minimize, the menthol-like aftertaste and prolonged sweet aftertastes which have plagued many of the dihydrochalcones prepared heretofore. The present invention seeks to realize these goals.

wherein R is a lower alkyl of from 1 to 3 carbons inclusive, X is hydrogen or hydroxy, and M+ is a physiologically acceptable cation. These materials may be named 2,3'6-trihydroxy and 2,3'-dihydroxy-4-(3-sulfo-4,5-dihydroxyhexoxy)-4'-alkoxydihydrochalcone salts. These materials impart sweet flavors to foods, beverages, medicaments and other comestibles.

DETAILED DESCRIPTION OF THE INVENTION

The Compounds

The compounds of the present invention have the structure shown in General Formula I. In that Formula R is an alkyl, more particularly a 1, 2 or 3 carbon alkyl that preferably is linear, i.e., methyl, ethyl or n-propyl. Methyl is the most preferred R.

X is either hydrogen or hydroxy, with hydroxy being preferred. M+ is a physiologically acceptable cation. As used herein, a "physiologically acceptable cation" is defined to include ammonium and the cations of the third and fourth period metals wich are non-toxic, i.e., Na(I), K(I), Mg(II), Ca(III), Al(III), Mn(II), Fe(III), Cu(II) and Zn(II). Preferred cations are the cations of the third and fourth period group I and II metals, i.e, Na(I), K(I), Mg(II), and Ca(II), with K being the most preferred metal cation. In the structural formulas of this specification and claims, the divalent calcium cation will be shown as ½ Ca++ to indicate a charge balance with the monovalent sulfo group. In actual practice, of course, the Ca++ is associated with two monovalent dihydrochalcone groups. A most preferred compound is that material of Formula I wherein R is —CH$_3$, M+ is K+ and X is —OH.

Preparation.

The materials of General Formula I are conveniently formed, in a general sense, by substituting the 7 position of the flavanones shown in General Formula II

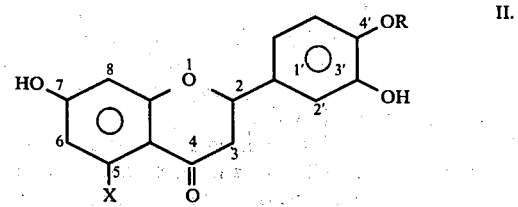

with the electrophilic addition reagent, epoxysultone and thereafter converting the epoxysulfonate to the required diol configuration and the flavanone to the desired dihydrochalcone. The flavanones include hesperetin and its X equals hydrogen and R equals $C_2H_5$ or $C_3H_7$ equivalents. Epoxysultone has a formula

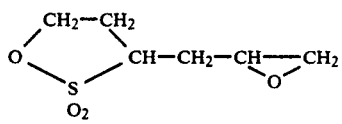

and is the subject of patent applications of Wang et al U.S. Ser. No. 863,117 filed on Dec. 22, 1977 (now abandoned) and U.S. Ser. No. 929,622 filed on July 31, 1978. Epoxysultone, per se, is not a part of the present invention. Its preparation is shown in the examples.

This preparative scheme may be shown as follows:

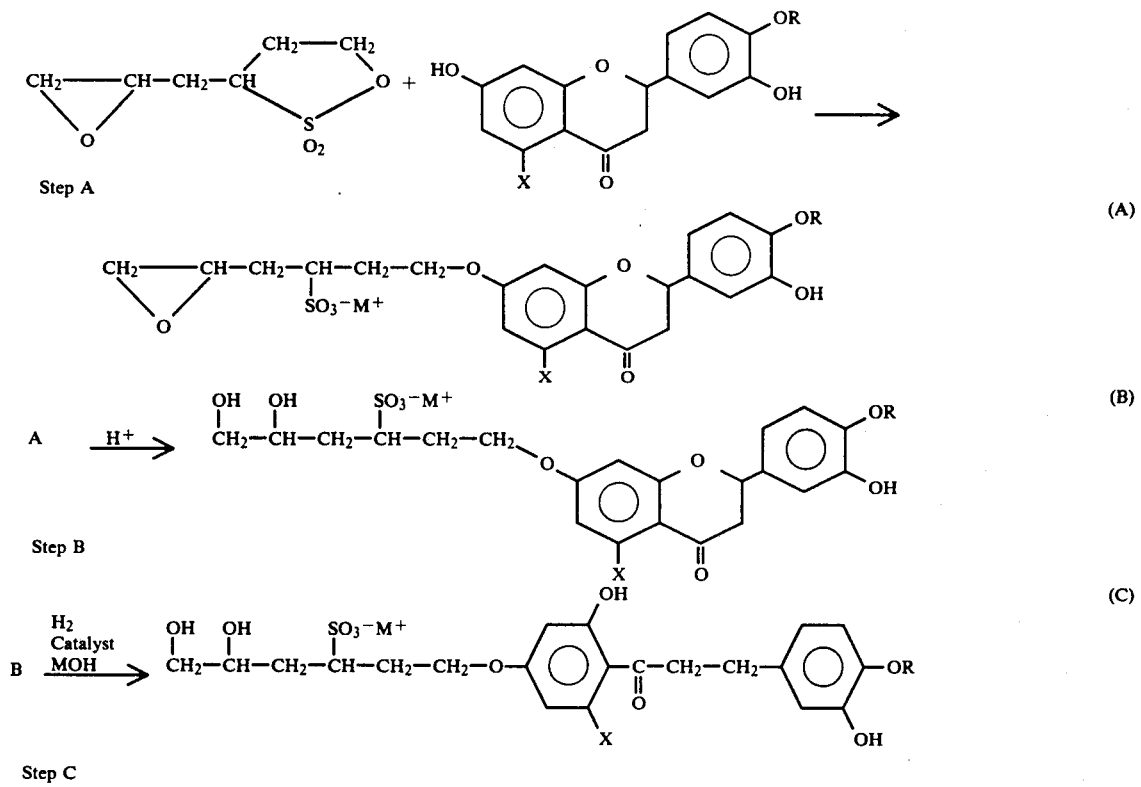

from 10° C. to 40° C. for times of from 5 to 70 hours. Time, of course, is inversely proportional to temperature. The mixture is generally stirred and blanketed with an inert gas atmosphere. The epoxysultone addition product may be recovered by simple evaporation of solvent and need not be purified.

The conversion of the epoxysulfonate group to the required diol configuration (Step B, above) is effected by treating an aqueous solution of the epoxysulfonate with a catalytic amount of nonoxidizing strong mineral acid, such as HCl, $H_2SO_4$, $HClO_4$, HBr, or the like. Preferably, this is carried out in the presence of acetic acid as cosolvent. Generally, somewhat elevated temperatures, such as 35° C. to 100° C. and preferably 45° C. to 80° C. are employed and require relatively long reaction times such as from 10 to 100 hours and preferably 15 to 80 hours to complete. The "diol" product is recovered from the reaction product by conventional workup such as by evaporation of solvent, resolution of solids, extraction (repeated 3-10 times) of this solution with a water-immiscible organic liquid extraction medium such as ethyl acetate or chloroform or the like and evaporation to dryness of the aqueous phase containing the "diol". While more strenuous conditions could probably be devised for each of the reaction steps set forth, they have been considered generally less favorable because of their potential for increased side product formation and lower yields.

The opening and hydrogenation of the flavanones to the dihydrochalcone configuration (Step C, above) is carried out with molecular hydrogen and a suitable catalyst. Mild conditions, such as a gross excess of hydrogen (for example 10 to 100 psi), dilute aqueous base such as 1 to 8 molar, preferably 2 to 6 molar alkali metal The addition of epoxysultone to the flavanone 7 position (Step A, above) is carried out as follows. Epoxysultone and the flavanones are combined in a liquid phase polar aprotic reaction medium. Suitable media include N,N-dimethylformamide (DMF), dimethylsulfoxide, hexamethylphosphoramide, and the like with DMF generally being preferred. The molar amounts of flavanones and epoxysultone are about equal with slight excesses of the flavanones, i.e., 1 to 1.5, preferably 1 to 1.4 and most preferably 1 to 1.2 equivalents of flavanones per mole of epoxysultone being preferred. Excess epoxysultone can give rise to unwanted multiple substitution and is to be avoided.

An acid acceptor, such as an alkali metal carbonate, bicarbonate or hydroxide, and preferably $Na_2Co_3$ or $K_2CO_3$, is present during the epoxysultone addition reaction. This material is generally present in a molar amount about equal to the moles flavanone —i.e., 1-1.5 equivalents, basis epoxysultone. The reaction is carried out under moderate conditions such as temperatures of hydroxide, particularly KOH or NaOH and a noble metal catalyst such as palladium or platinum, (preferably palladium) preferably supported such as upon charcoal or the like. Times of from a few hours to about 30 hours, with temperatures of from room temperature (20° C.) to say 35° C. may be employed. As earlier noted, more strenuous conditions may be employed, if desired.

Following hydrogenation and opening, the product is recovered, such as by filtration to remove catalyst, evaporation to dryness and chromatography, such as by liquid chromatography or other equivalent chromatographic techniques, or by careful recrystallization.

The starting flavanones employed in this synthesis include hesperetin and its X and R substituted equivalents. Hesperetin (X=OH, R=CH₃) is available commercially. The other flavanones are less common and generally must be prepared. One preparative route for these flavanones involves condensation of an appropriately protected hydroxyacetophenone with an appropriately protected 3-hydroxy-4-alkoxybenzaldehyde in the presence of base to give a chalcone which is then converted to the desired flavanone by treatment with strong acid.

This route may be shown as follows:

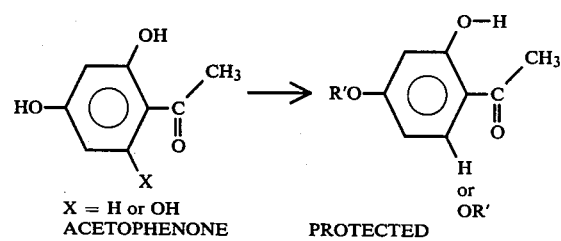

X = H or OH
ACETOPHENONE

PROTECTED ACETOPHENONE
wherein R' is a protecting group, such as benzyl.

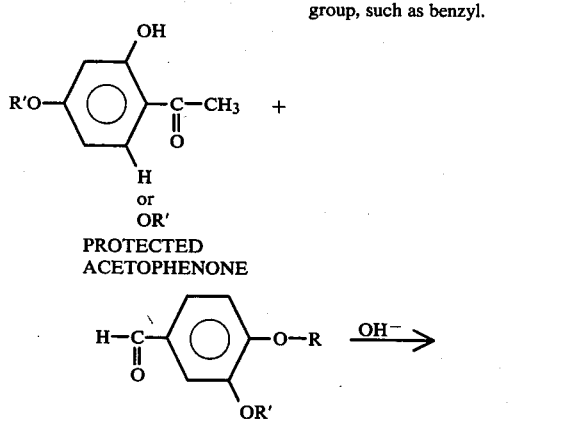

PROTECTED ACETOPHENONE

PROTECTED BENZALDEHYDE
wherein R' is a protecting group such as benzyl.

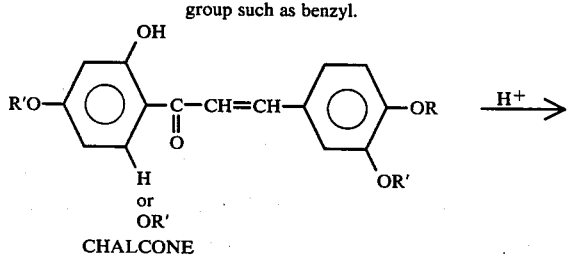

CHALCONE

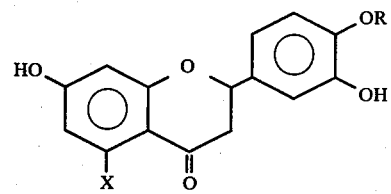

FLAVANONE

These steps can be carried out with process conditions and reagents known to those skilled in the art.

The protected hydroxyacetophenone derivatives, such as 2-hydroxy-4,6-dibenzyloxyacetophenone and 2-hydroxy-4-benzyloxyacetophenone, are prepared from the requisite commercially available hydroxyacetophenones by treatment with a reagent such as a benzyl halide, particularly benzyl bromide or iodide or chloride (1.00–1.25 equivalent based upon the number of hydroxyl groups to be reacted) at 25°–80° C. in polar aprotic liquid phase media. Suitable media include N,N-dimethylformamide (DMF), dimethyl sulfoxide, hexamethylphosphoramide, and the like. An acid acceptor, such as a metal bicarbonate, carbonate, or hydroxide, especially an alkali metal such as K⁺ of a bicarbonate, carbonate or hydroxide, is also added to the reaction mixture in an amount of from 0.8 to 1.5 equivalents per mole of hydroxyl group being protected. Generally, long reaction times, such as at least 12 hours, are employed with these mild conditions. The most preferred method for preparing the protected hydroxyacetophenones involves the use of benzyl chloride (1.1 equivalent) and K₂CO₃ (1.0 equivalent) in DMF at 25°–40° C. Under these conditions the reactions are complete within 3–4 days, with product isolation being carried out by means of a standard aqueous workup.

The protected 4-alkoxy-3-hydroxybenzaldehydes, needed for condensation with the protected hydroxyacetophenones, are prepared by a two-step process from 3,4-dihydroxybenzaldehyde (protocatechualdehyde, commercially available). The first step, which is the preparation of the intermediate 4-alkoxy-3-hydroxybenzaldehydes, involves the treatment of the dihydroxybenzaldehyde with 1.0–1.1 molar equivalents of a 1–3 carbon alkyl halide (especially iodide) in a plar aprotic solvent, such as DMF, at room temperature or slightly above (15°–40° C.). An acid acceptor, such as an alkali metal carbonate, bicarbonate or hydroxide and preferably K₂CO₃, in a molar amount about equal to the moles of alkyl halide is required for this reaction. When carried out under these mild conditions, the hydroxyl group at the 4-position, being somewhat more reactive than the hydroxyl group at the 3-position, is alkylated almost exclusively. Protection of the remaining hydroxyl is then effected preferably by benzylation such as at 25°–50° C. with either benzyl chloride or benzyl bromide in DMF or a similar solvent containing 1.0–1.2 molar equivalents of K₂CO₃. This completes the preparation of the 4-alkoxy-3-benzyloxybenzaldehydes or their otherwise protected equivalents.

The aldol condensation of the protected hydroxyacetophenones with the 4-alkoxybenzaldehydes, to afford a chalcone, is best carried out with a slight molar excess (preferably 1.1 to 1.5 molar equivalents, basis acetophenone) of benzaldehyde in a lower alkanol (methanol, ethanol, isopropanol) at room temperature to 75° C. A large excess (10-20 molar equivalents) of a strong base, such as NaOH, KOH, NaOEt, or t-BuOK, is needed in order for this reaction to proceed at a reasonable rate. The preferred method for conducting this aldol condensation is to utilize about 1.25 molar equivalents of the benzaldehyde and about 15 molar equivalents of NaOEt in absolute ethanol (10-15 ml/mmol of acetophenone) at 20°-30° C. Under these conditions, the condensation is complete within 72 hours. The chalcone products may be isolated, after neutralization of the reaction mixture, by either a standard aqueous workup or by evaporating the reaction mixture to dryness and then extracting the product from the salts. Purification is carried out by recrystallization, with toluene being the preferred solvent.

The chalcones, when protected as preferred with benzyl groups, undergo debenzylation with concomitant cyclization to the flavanones upon treatment with excess very strong mineral acid. Aqueous HI or HBr (10-12 molar equivalents) in glacial acetic acid (20-60 ml/mmol of chalcone) are preferred acids and are employed at mildly elevated temperatures (30°-100° C.). In general, these reactions proceed rather poorly with other mineral acids, such as HCl, $H_2SO_4$, or $HClO_4$. The product flavanones are isolated, as a mixture with the resulting benzyl halide co-product, by a standard aqueous workup. Purification is best accomplished by chromatographic techniques, such as thin layer chromatography or column chromatography. All of these reactions may be advantageously carried out with stirring and under an inert gas atmosphere.

The dihydrochalcone products of this invention are sweet. They may be used as non-sucrose sweeteners for edibles such as foods, medicaments and beverages. In this use they may be admixed such as by dissolving or dry mixing with the edible as is appropriate. In this use they exhibit a sweetness substantially greater than sucrose and thus should be used in an amount about 1/100-1/1000 that of sucrose. Thus, amounts of from about 0.2 to 0.005% by weight (basis edibles) may be employed.

The present invention will be further shown by the following examples. These are intended to exemplify the invention and are not to be construed as limiting its scope.

EXAMPLES

Preparation of Precursors

I. Epoxysultone

Propane sultone, 3.84 g, was dissolved in 200 ml of freshly distilled THF in a 500-ml, round-bottomed flask. The flask was capped, deaerated and cooled with a dry ice-acetone bath for one-half hour. Under argon, n-butyllithium in hexane (14.4 ml, 1.10 equiv.) was added over five minutes. After stirring for five minutes at −78° C., alkyl bromide (3.4 ml, 1.25 equiv.) was added over five minutes. The clear, colorless solution was stirred under argon at −78° C. for two hours. The reaction mixture was poured into a separatory funnel containing 500 ml of ethyl acetate and 250 ml of water, and shaken. Two phases formed. The aqueous phase was discarded. The organic phase was washed with brine, dried over $MgSO_4$ and evaporated to remove solvent. The product was 4.81 g (94% yield) of a clear, viscous oil which was shown to be 1-oxa-2-thia-3-(2-propenyl)cyclopentane 2,2-dioxide

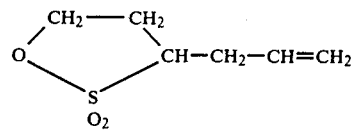

by H'NMR spectrum in $CDCl_3$.

This material (3.70 g) was epoxidized by dissolving in 100 ml of dry methylene chloride, adding m-chloroperbenzoic acid (85% pure, 6.96 g, 1.5 equiv.) and heating at reflux for two days. The reaction mixture was cooled, and filtered to remove some white solid which had formed. The liquid was washed with 20% $NaHSO_3$ (100 ml portions, five times), saturated $NaHCO_3$ (250 ml portions, four times), brine (250 ml portions, two times), dried over $MgSO_4$ and evaporated to dryness. A crude white material (3.18 g) was recovered, and subjected to column chromatography on a silica gel colum with chloroform as eluent. A fraction was taken and evaporated to yield 1.7 g (42% yield). The clear oil which resulted was shown by TLC to be pure, and by elemental analysis and NMR to be the desired epoxysultone of formula

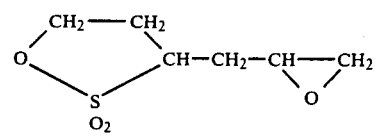

II. Flavanones by Condensing Aldehydes and Acetophenones

A. Preparation of Unprotected Aldehyde Reactants (1) A solution of 2.76 g (20.0 mmoles) of 3,4-dihydroxybenzaldehyde and 2.76 g (20.0 mmoles) of anhydrous potassium carbonate and 3.45 g (22.0 mmoles) of ethyl iodide is prepared in 15 ml of dry DMF and stirred under argon for 24 hours at room temperature. The reaction mixture is poured into 50 ml of water, saturated with sodium chloride and extracted thrice with diethyl ether. The ether extracts are washed with water, and brine, dried and concentrated to yield the ethoxyaldehyde as dark crystals.

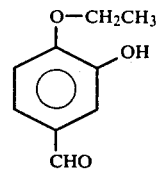

(2) The reaction is repeated using 3.74 g (22.0 mmoles) of n-propyl iodide in place of ethyl iodide to yield the propoxyaldehyde

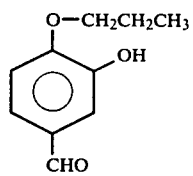

(3) The reaction is repeated using 3.12 g (22.0 mmoles) of methyl iodide in place of ethyl iodide to yield the methoxyaldehyde.

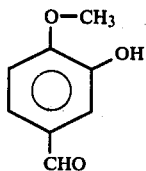

B. Preparation of 4-Alkoxy-3-benzyloxybenzaldehyde

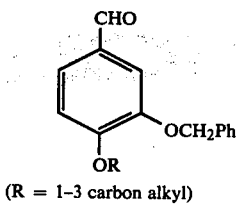

(R = 1-3 carbon alkyl)

4-Alkoxy-3-hydroxybenzaldehyde (1.0 equiv.), benzyl chloride (1.2 equiv.), and $K_2CO_3$ (1.2 equiv.) are stirred in anhydrous DMF at 35° C. for 72 hours. The reaction is poured into ether and the resulting mixture washed thoroughly with $H_2O$, dilute aqueous KOH (until the ethered solution is free of unreacted hydroxybenzaldehyde as determined by TLC), $H_2O$ again, and finally brine. Evaporation affords crude 4-alkoxy-3-benzyloxybenzaldehyde which is generally suitable for use, as is, in the condensation reaction. Additional purification may be achieved by silica gel column chromatography.

C. Preparation of Protected Acetophenones (1) Preparation of 2-Hydroxy-4,6-dibenzyloxyacetophenone

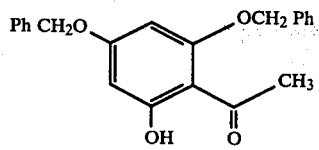

2,4,6-Trihydroxyacetophenone (16.8 g, 0.10 mol, Aldrich Chemical Company) and benzyl chloride (27.8 g, 0.22 mol) was dissolved in 200 ml of dry DMF and the solution was thoroughly purged with argon. The mixture was treated with 27.6 g (0.20 mol) of $K_2CO_3$ and stirred at 35° C. for 84 hours. The reaction was poured into ether (1200 ml) and resulting mixture washed with $H_2O$ (1×500 ml), 5% aqueous KOH solution (3×500 ml), $H_2O$ (1×500 ml), and saturated NaCl solution (1×250 ml). After dring over $MgSO_4$, the ethereal solution was evaporated to afford 27.4 g of crude product as an off-white granular solid. Trituration of the crude product with ether (100 ml), followed by filtration and drying in vacuo provided 13.5 g (38.8%) of 2-hydroxy-4,6-dibenzyloxyacetophenone as a white solid, mp 101°-102° C., i.e.,

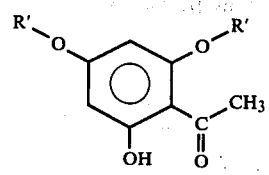

wherein R' is benzyl.

The product was homogeneous by silica gel TLC ($CHCL_3$ elution) and the assigned structure was verified by both NMR and elemental analysis.

(2) Preparation of 2-hydroxy-4-benzyloxyacetophenone

The reaction of (1) above is repeated using 1.1 molar equivalents of benzyl chloride, 1.0molar equivalent of $K_2CO_3$, and substituting for the above acetophenone,2,4-dihydroxyacetophenone

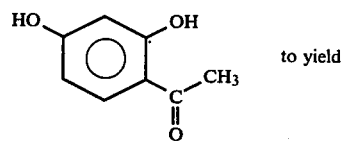

to yield

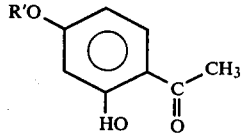

D. Preparation of 2-Hydroxy-3',4,6-tribenzyloxy-4'-alkoxychalcone

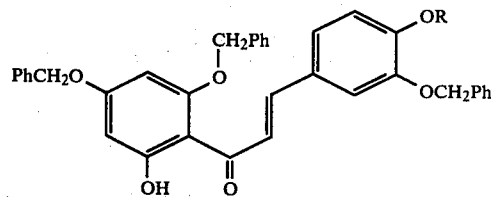

(R = 1-3 carbon alkyl)

A 500-ml, 3-neck flask, equipped with overhead stirrer, is charged with 9.04 g (25.9 mmol) of 2-hydroxy-4,6-dibenzyloxyacetophenone, 1.25 equiv. (32.4 mmol) of 4-alkoxy-3-benzyloxybenzaldehyde, and 300 ml of absolute ethanol. The mixture is stirred until a homogeneous solution is obtained, at which point 26.4 g (0.39 mol) of powdered sodium ethoxide is added. The reaction is stirred at room temperature under argon for 72 hours and then quenched by the addition of 39 g (0.65 mol) of glacial acetic acid.

The reaction mixture is evaporated to complete dryness and triturated for 30 minutes with 500 ml of boiling tetrahydrofuran and filtered. The trituration is repeated twice, and the combined filtrates are evaporated to dryness. Recrystallization from boiling toluene affords chalcone (40-65%) as a bright yellow crystalline solid. The identity and homogeneity of the product are determined by silica gel TLC (ethyl acetate-hexane, 1:1), proton NMR, and elemental analysis.

E. Preparation of 3',5,7-Trihydroxy-4'-alkoxyflavanone

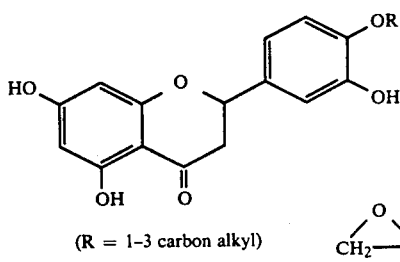

(R = 1–3 carbon alkyl)

A 1.0 mmol sample of 2-hydroxy-3',4,6-tribenzyloxy-4'-alkoxychalcone is dissolved in 40 ml of glacial acetic acid at 60° C. and treated with 2 ml of 48% aqueous HBr. The yellow solution becomes deep reddish-orange upon addition of the acid. After stirring 24 hours at this temperature, the reaction is poured into H$_2$O (200 ml) and the resulting aqueous mixture extracted with an equal volume of ethyl acetate. The organic extract is washed with H$_2$O (2×100 ml), 5% aqueous NaHCO$_3$ solution (2×100 ml), H$_2$O (1×100 ml), saturated aqueous NaCl solution (1×50 ml), and dried over MgSO$_4$. Evaporation affords the crude flavanone admixed with three equivalents of benzyl bromide.

Silica gel column chromatography (elution with ethyl acetate-hexane, 1:1) affords flavanone (30–60%) as an off-white crystalline solid, which may be further purified by preparative high-pressure liquid chromatography (HPLC), as described in DuBois et al., J. Agric. Food Chem., 25, 763 (1977), if desired. Product identity and homogeneity are deterined by silica gel TLC (ethyl acetate-hexane, 1:1), proton NMR, and elemental analysis.

F. The coupling, exemplified by parts D. and E., is repeated four more times varying the aldehyde among the three materials of Part A of this preparation and the two acetophenones of Part B, so, with the materials of D. and E., as to yield the six possible flavanones of General Formula II which can result when X is H or OH and R is CH$_3$, C$_2$H$_5$ or C$_3$H$_7$.

EXAMPLE I

Preparation of Sweetener Wherein X is OH, R is CH$_3$ and M$^{30}$ is K+

The epoxysultone (0.35 g) prepared above as dissolved in 4 ml of dry DMF. Hesperetin (0.66 g, 1.1 equivalents-Sigma Chemical) was added. The mixture was stirred for ten minutes under argon at room temperature. Potassium carbonate (0.30 g, 1.1 equivalents) was added and the mixture was stirred at room temperature under argon for 42 hours. The mixture was filtered to remove solids and the filtrate evaporated to give a thick oil which by HPLC was seen to be essentially pure hesperetin epoxysulfonate contaminated by a small amount of unreacted hesperetin.

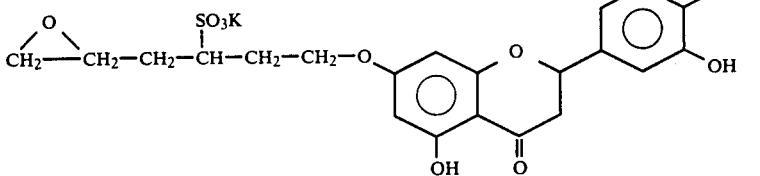

The epoxysulfonate was placed in a 250 ml flask. Glacial acetic acid (17.5 ml) and 0.05 M sulfuric acid (40 ml) were added and the mixture maintained at 60° C. for 46 hours, cooled, and evaporated on a rotary evaporator. The residue was dissolved in 250 ml of water, washed with five 250-ml portions of ethyl acetate and evaporated to about 40 ml. By HPLC, quantitative reaction of the epoxide group had been achieved.

The product of the ring opening was then placed under argon in a Parr hydrogenation apparatus. The apparatus was charged with 32 psi of hydrogen, a 5% palladium on charcoal catalyst (0.3 g) and dilute aqueous KOH (4.02 M, 5.0 ml). After 17 hours, at room temperature, the reaction product was removed, filtered through Celite, acidified with HCl, evaporated to dryness, redissolved in water, and separated by preparative HPLC into its components. One component, which isolated 99% pure, was studied by NMR, and elemental analysis and confirmed to be the dihydroxyhexoxy dihydrochalcone;

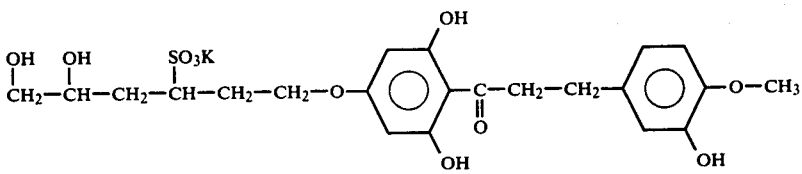

EXAMPLE II

Preparation of Dihydrochalcones Wherein X is H, R is CH$_3$ and M+ is K+

The preparation of Example 1 is repeated with one modification. In place of 1.1 equivalents of hesperetin, an equimolar amount of the flavanone of General Formula II wherein X is H and R is CH$_3$ and prepared at C(2) above is employed. This gives rise to the dihydrochalcone of Formula I wherein X is H, R is CH$_3$ and M+ is K+.

EXAMPLE III

Preparation of Dihydrochalcones Wherein X is H and OH and R is C$_2$H$_5$ and C$_3$H$_7$ The preparation of Example I is repeated four more times. Each time, a new flavanone prepared at C. above is employed. This results in the formation of the dihydrochalcones in accord with Formula I with the following substituents:

| R | X | M+ |
|---|---|---|
| $C_2H_5$ | OH | $K^+$ |
| $C_2H_5$ | H | $K^+$ |
| $C_3H_7$ | OH | $K^+$ |
| $C_3H_7$ | H | $K^+$ |

EXAMPLE IV

In the preceding examples, the potassium salt is formed; this corresponds to the base employed during sultone alkylation ($K_2CO_3$). Other salts are formed by varying the base among $Na_2CO_3$, $CaCO_3$ and the like (with the corresponding hydroxide being employed during the hydrogenation), or by passage of a solution of dihydrochalcone over a strong acid ion exchange resin followed by titration with the desired ammonium or metal hydroxide, or often by merely adding an excess of the desired cation to a solution of dihydrochalcone and precipitating the desired salt. In a typical preparation, a solution of the potassium salt formed in Example I is passed over a freshly washed and regenerated bed of the acidic ion exchange resin Amberlite$^R$ 120 (Rohm and Hass) in the acid form. This forms the free acid. The solution of free acid is separated into three parts, each of which is neutralized: the first, by the addition of one equivalent of $Ca(OH)_2$; the second, by the addition of one equivalent of HaOH; and, the third by the addition of one equivalent of $NH_4OH$.

EXAMPLE V

The products of Examples I through IV exhibit the properties of being soluble in water and other aqueous systems and of being sweet when tasted. Accordingly, they are added to the following edibles, an unsweetened cola beverage, an unsweetened lemonade base, an orange soda containing one-half its normal amount of sugar, a diet beverage containing one-fifth its normal amount of saccharin, a cough medicine and a powder for making gelatin desserts. In each application the compounds impart a desirable sweet flavor.

What is claimed is:

1. A dihydroxyhexoxy substituted dihydrochalcone compound represented by the structural formula

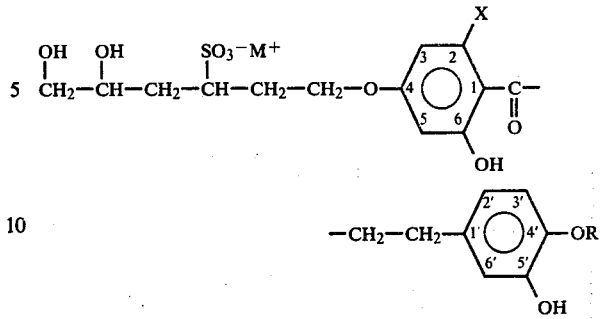

wherein R is a lower alkyl of from one to three carbon atoms inclusive, X is hydrogen or hydroxy, and M+ is a physiologically acceptable cation.

2. The dihydrochalcone compound of claim 1 wherein R is methyl, X is hydrogen and $M^{30}$ is selected from the group consisting of $Na^+$, $K^{30}$ and $\frac{1}{2}Ca^{++}$.

3. The dihydrochalcone compound of claim 1 wherein R is ethyl, X is hydrogen and $M^{30}$ is selected from the groups consisting of $Na^{30}$, $K^+$ and $\frac{1}{2}Ca^{++}$.

4. The dihydrochalcone compound of claim 1 wherein R is n-propyl, X is hydrogen and M+ is selected from the group consisting of $Na^+$, $K^+$ and $\frac{1}{2}Ca^{++}$.

5. The dihydrochalcone compound of claim 1 wherein R is methyl and X is hydroxy.

6. The dihydrochalcone compound of claim 5 wherein M+ is selected from the groups consisting of $Na^+$, $K^+$ and $\frac{1}{2}Ca^{++}$.

7. The dihydrochalacone compound of claim 5 wherein M+ is $K^+$.

8. The dihydrochalcone compound of claim 1 wherein R is ethyl, X is hydroxy, and M+ is selected from the group consisting of $Na^+$, $K^+$ and $\frac{1}{2}Ca^{++}$.

9. The dihydrochalcone compound of claim 1 wherein R is n-propyl, X is hydroxy and M+ is selected from the group consisting of $Na^+$, $K^+$ and $\frac{1}{2}Ca^{++}$.

10. A sweetened comestible material comprising an edible material having admixed therewith, as a sweetening agent, a dihydrochalcone compound of claim 1 in an amount sufficient to sweeten said edible material.

11. A sweetened comestible material comprising an edible material having admixed therewith as a sweetening agent, the dihydrochalcone compound of claim 7 in an amount sufficient to sweeten said edible material.

* * * * *